United States Patent
Kim

(10) Patent No.: US 10,772,505 B2
(45) Date of Patent: Sep. 15, 2020

(54) BIO-INFORMATION MEASURING APPARATUS AND BIO-INFORMATION MEASURING METHOD

(71) Applicant: SAMSUNG ELECTRONICS CO., LTD., Suwon-si (KR)

(72) Inventor: Dong Ho Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 142 days.

(21) Appl. No.: 15/945,010

(22) Filed: Apr. 4, 2018

(65) Prior Publication Data
US 2019/0150746 A1 May 23, 2019

(30) Foreign Application Priority Data

Nov. 17, 2017 (KR) .................. 10-2017-0154234

(51) Int. Cl.
*A61B 5/1455* (2006.01)
*A61B 5/00* (2006.01)
(Continued)

(52) U.S. Cl.
CPC .......... *A61B 5/0075* (2013.01); *A61B 5/0082* (2013.01); *A61B 5/01* (2013.01); *A61B 5/1455* (2013.01); *A61B 5/14532* (2013.01); *A61B 5/14546* (2013.01); *A61B 5/681* (2013.01); *A61B 5/6824* (2013.01); *A61B 5/6831* (2013.01); *A61B 5/6843* (2013.01); *A61B 5/6885* (2013.01); *A61B 5/721* (2013.01); *A61B 5/742* (2013.01); *A61B 2560/0252* (2013.01); *A61B 2562/0247* (2013.01); *A61B 2562/0252* (2013.01); *A61B 2562/0261* (2013.01); *A61B 2562/0271* (2013.01); *A61B 2562/04* (2013.01); *A61B 2562/06* (2013.01)

(58) Field of Classification Search
None
See application file for complete search history.

(56) References Cited

U.S. PATENT DOCUMENTS 7,299,079 B2 11/2007 Rebec et al.
7,761,129 B2 7/2010 Van Der Voort et al.
(Continued)

FOREIGN PATENT DOCUMENTS

EP 2400288 A1 12/2011
EP 3318854 A1 5/2018

OTHER PUBLICATIONS

Communication dated Feb. 1, 2019, from the European Patent Office in counterpart European Application No. 18176051.3.
(Continued)

*Primary Examiner* — Eric F Winakur
*Assistant Examiner* — Marjan Fardanesh
(74) *Attorney, Agent, or Firm* — Sughrue Mion, PLLC

(57) ABSTRACT

Provided is a bio-information measuring apparatus. According to an aspect, the bio-information measuring apparatus includes: an optical module comprising a light source configured to emit light onto or toward an object, and a detector configured to detect light reflected or scattered from the object; a pressure sensor configured to measure pressure between the optical module and the object; and a processor configured to restore a spectrum based on the detected reflected or scattered light, and to correct the restored spectrum based on the measured pressure.

18 Claims, 15 Drawing Sheets

(51) Int. Cl.
    *A61B 5/145*     (2006.01)
    *A61B 5/01*     (2006.01)

(56) References Cited

U.S. PATENT DOCUMENTS

| | | |
|---|---|---|
| 8,160,666 B2 | 4/2012 | Rebec et al. |
| 8,452,359 B2 | 5/2013 | Rebec et al. |
| 8,676,284 B2 | 3/2014 | He |
| 9,173,447 B2 | 11/2015 | Boakye |
| 9,554,735 B2 | 1/2017 | Rebec et al. |
| 9,603,521 B2 | 3/2017 | Cho et al. |
| 9,642,538 B2 | 5/2017 | Newberry |
| 9,713,447 B2 | 7/2017 | Caduff et al. |
| 2004/0092804 A1 | 5/2004 | Rebec et al. |
| 2008/0045820 A1 | 2/2008 | Rebec et al. |
| 2008/0045821 A1 | 2/2008 | Rebec et al. |
| 2008/0200781 A1 | 8/2008 | Van Herpen et al. |
| 2013/0237797 A1 | 9/2013 | Müller et al. |
| 2013/0261406 A1 | 10/2013 | Rebec et al. |
| 2015/0297123 A1 | 10/2015 | Khokhoev et al. |
| 2016/0089088 A1 | 3/2016 | Kim et al. |
| 2017/0143210 A1 | 5/2017 | Ikebe |
| 2018/0128680 A1 | 5/2018 | Kim |
| 2018/0146855 A1 | 5/2018 | Anikanov et al. |

OTHER PUBLICATIONS

Tai-Sheng Yeh et al., "A Low Cost LED Based Spectrometer", Journal of the Chinese Chemical Society, Jun. 21, 2006, vol. 53, No. 5, pp. 1067-1072. (6 pages total).

BIO-INFORMATION MEASURING APPARATUS AND BIO-INFORMATION MEASURING METHOD

CROSS-REFERENCE TO RELATED APPLICATION(S)

This application claims priority from Korean Patent Application No. 10-2017-0154234, filed on Nov. 17, 2017, in the Korean Intellectual Property Office, the entire disclosure of which is incorporated herein by reference for all purposes.

BACKGROUND

1. Field

The exemplary embodiments relate generally to an apparatus and method for measuring bio-information, and more particularly to technology for improving accuracy of measurement of bio-information in a non-invasive manner by using a near-infrared spectrum.

2. Description of the Related Art

Recently, research is being conducted on a method of measuring bio-information, such as blood glucose, in a non-invasive manner by using Raman spectroscopy or near-infrared spectroscopy. A general bio-information measuring device is composed of a light source, which emits light onto an object, and a detector which detects light reflected or scattered from the object, and measures an in vivo component, such as blood glucose, cholesterol, calories, and the like, by skin near-infrared absorption spectrum analysis or Raman scattering analysis. Such general bio-information measuring devices use a method of obtaining a spectrum by using a broadband light source, grating, narrow band filter, or the like, of a tungsten lamp and the like.

SUMMARY

In one general aspect, there is provided a bio-information measuring apparatus including: an optical module comprising a light source configured to emit light onto an object, and a detector configured to detect light scattered from the object; a pressure sensor configured to measure pressure between the optical module and the object; and a processor configured to restore a spectrum based on the detected optical signal, and to correct the restored spectrum based on the measured pressure.

In this case, the light source may be formed to be an array of a plurality of light sources including at least one of a light emitting diode (LED), a laser diode, and a fluorescent body; and the processor may sequentially drive the plurality of light sources by time-dividing the light sources The optical module may include a direction change part configured to change a direction of light emitted by the light source, so that the light may be directed toward the object.

In addition, the bio-information measuring apparatus may further include an external frame which supports the optical module and inwardly receives the light source and the detector of the optical module.

One or more of the pressure sensors may be disposed on one surface of the direction change part or on one surface of the external frame.

When two or more of the pressure sensors are disposed, the processor may determine a state of contact between the optical module and the object based on a difference between pressure values measured by each of the pressure sensors.

Further, the bio-information measuring apparatus may further include an output part configured to output warning information in response to the state of contact not being normal based on the determination.

The processor may determine an event occurrence time based on a change of the pressure values continuously measured by the pressure sensors.

In response to a difference between a pressure value at a reference time and a pressure value at a measured time exceeding a threshold value, the processor may determine that an event occurs.

The processor may correct a spectrum at the event occurrence time based on a correction model.

Moreover, the bio-information measuring apparatus may further include a temperature sensor configured to measure temperature of the object when the optical module detects an optical signal from the object.

Among a plurality of reference spectrums pre-measured for each temperature, the processor may determine a reference spectrum for use in restoring the spectrum based on the measured temperature.

The processor may measure bio-information, including one or more of blood glucose, triglyceride, cholesterol, calories, protein, and uric acid, based on the corrected spectrum.

In another general aspect, there is provided a bio-information measuring method, including: by an optical module, emitting light onto an object and detecting light scattered from the object; measuring pressure between the optical module and the object by a pressure sensor; restoring a spectrum based on the detected optical signal; and correcting the restored spectrum based on the measured pressure.

In addition, bio-information measuring method may further include: determining a state of contact between the optical module and the object based on a difference between pressure values measured by two or more pressure sensors; and in response to the state of contact not being normal based on the determination, outputting warning information.

The bio-information measuring method may include determining an event occurrence time based on a change of the pressure values continuously measured by the pressure sensors; and the correcting of the restored spectrum may include correcting a spectrum at the event occurrence time based on a correction model.

The determining of the event occurrence time may include determining that an event occurs in response to a difference between a pressure value at a reference time and a pressure value at a measured time exceeding a threshold value.

Further, the bio-information measuring method may further include: measuring temperature of the object when the optical module detects an optical signal from the object; and determining a reference spectrum based on the measured temperature.

Moreover, the bio-information measuring method may further include measuring bio-information, including one or more of blood glucose, triglyceride, cholesterol, calories, protein, and uric acid, based on the corrected spectrum.

In addition, the bio-information measuring method may further include outputting a measurement result of the bio-information.

Figure 1:
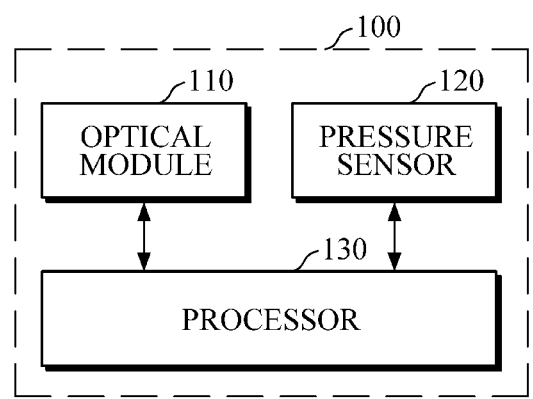
FIG. 1 is a block diagram illustrating a bio-information measuring apparatus according to an exemplary embodiment of the present disclosure.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Details of other embodiments are included in the following detailed description and drawings. Advantages and features of the present invention, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part', 'unit' or 'module', etc., should be understood as a unit that performs at least one function or operation and that may be embodied as hardware, software, or a combination thereof.

Hereinafter, embodiments of the bio-information measuring apparatus and the bio-information measuring method will be described in detail with reference to the accompanying drawings.

Figure 2A:
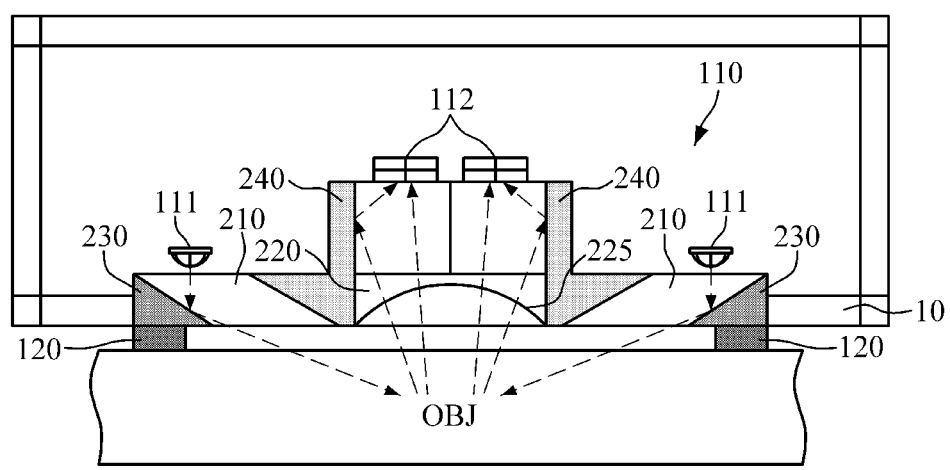
FIG. 2A is a cross-sectional view of a structure of an optical module according to an exemplary embodiment of the present disclosure.
Figure 2B:
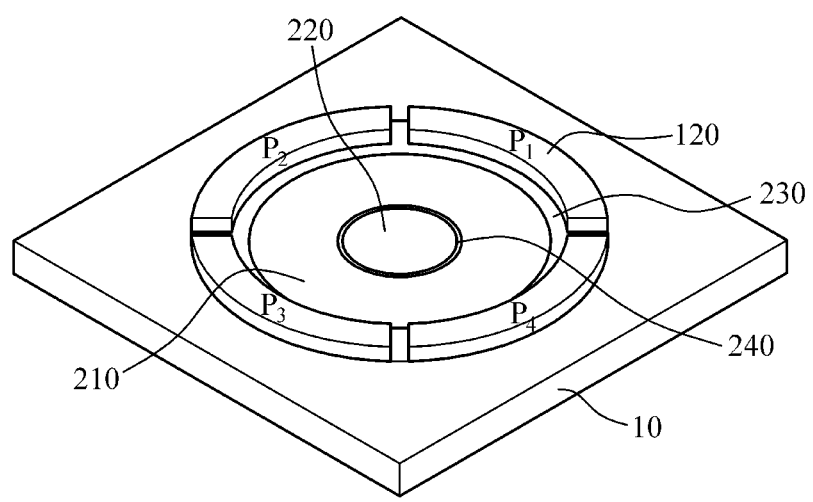
FIG. 2B is a perspective view of an optical module according to an exemplary embodiment of FIG. 2A.
Figure 2C:
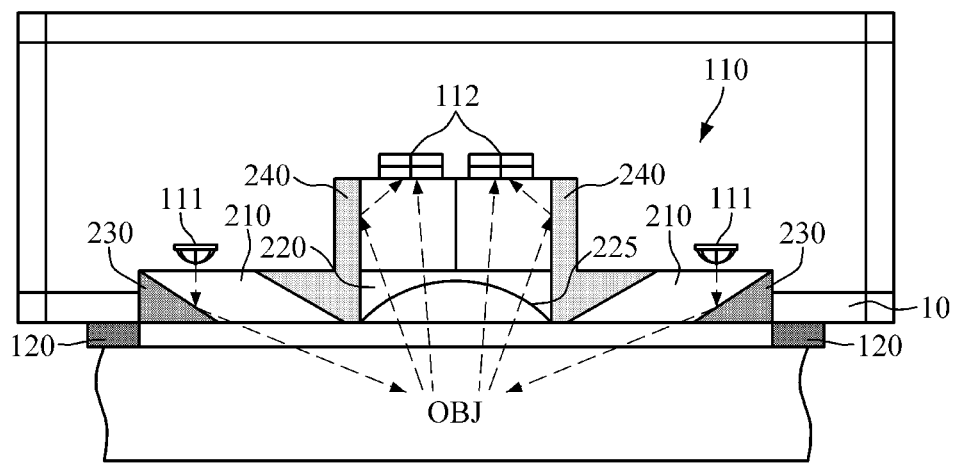
FIG. 2C is a cross-sectional view of a structure of an optical module according to another exemplary embodiment of the present disclosure.
Figure 2D:
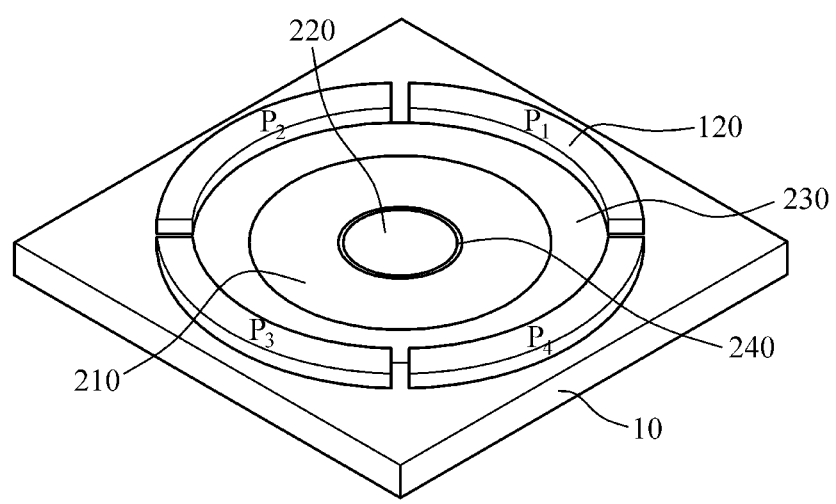
FIG. 2D is a perspective view of an optical module according to an exemplary embodiment of FIG. 2C.

FIG. 1 is a block diagram illustrating a bio-information measuring apparatus according to an exemplary embodiment of the present disclosure. FIG. 2A is a cross-sectional view of a structure of an optical module that is a hardware element, according to an exemplary embodiment of the present disclosure. FIG. 2B is a perspective view of an optical module according to an exemplary embodiment of FIG. 2A. FIG. 2C is a cross-sectional view of a structure of an optical module according to another exemplary embodiment of the present disclosure. FIG. 2D is a perspective view of an optical module according to an exemplary embodiment of FIG. 2C.

Referring to FIGS. 1 to 2D, the bio-information measuring apparatus 100 includes an optical module 110, a pressure sensor 120, and a processor 130. In this case, the optical module 110 and the processor 130 may function a spectrometer, may be integrally each other.

As shown in FIG. 2A, optical module 110 may include a light source 111, which emits light, e.g., an optical signal, onto or toward an object OBJ, and a detector 112, e.g., a hardware component such as a sensor, which detects light reflected or scattered from the object OBJ. Hereinafter, "reflected or scattered light" includes reflected light, scattered light, or both reflected light and scattered light.

The light source 111 may be a single light source, but is not limited thereto, and may be an array of a plurality of light sources. The light source 111 may be a light emitting diode (LED), a laser diode, a fluorescent body, and the like. The light source 111 may emit laser light or near-infrared light for use in Raman spectroscopy or near-infrared spectroscopy.

After the optical signal is emitted by the light source 111, the detector 112 may detect the light reflected or scattered from, the object OBJ depending on tissue properties of the object OBJ. The detector 112 may include a photodiode, an image sensor, and a photo-transistor. The detector 112 may convert the detected light into an electric signal, and may transmit the electric signal to the processor 130. The detector 112 may include a single photodiode, but is not limited thereto, and may include an array of a plurality of photodiodes.

Further, the optical module 110 may include a first light traveling part 210 which forms a light path for light emitted by the light source 111 to travel to the object. In addition, the optical module 110 may include a second light traveling part 220 which forms a light path for light reflected or scattered from the object to be directed toward the detector 112. The first light traveling part 210 and the second light traveling part 220 may be made of a light-transmissive material, e.g., glass.

Moreover, the optical module 110 may include a first direction change part 230 which changes a direction of light emitted by the light source 111 to a direction of the object OBJ. The direction change part 230 may change the direction of light emitted by the light source 111 to a portion to be examined, for example, a portion of a radial artery, or venous blood or capillary blood on a surface of the wrist, or any other parts of the body. Although exemplary embodiments describe the portion to be examined being a wrist, the wrist is merely an exemplary portion to be examined and these exemplary embodiments are not merely limited to examining the wrist, as other parts of the body may also be examined. Further, the optical module 110 may further include a second direction change part 240 which changes a direction of light, reflected or scattered from the object OBJ, to the detector 112. The first direction change part 230 and the second direction change part 240 are structural components which may be made of a non-light transmitting material, e.g., aluminum, and one surface of the first direction change part 230 and the second direction change part 240, e.g., a surface which faces the first light traveling part 210 and the second light traveling part 220, may be formed of an optical mirror which reflects light.

The light source 111 is controlled by the processor 130 to emit light, and a direction of the emitted light is changed by the first direction change part 230 to be absorbed into the object OBJ along the first light traveling part 210, as indicated by an arrow. Further, light scattered or reflected from the object OBJ depending on tissue properties of the object OBJ travels along the second light traveling part 220, in which a direction of some of the light is changed by the second direction change part 240, and is detected by the detector 112.

Referring to FIGS. 2A and 2B, on one surface of the optical module which contacts or faces the object, the first direction change part 230, the first light traveling part 210, the second direction change part 240, and the second light traveling part 220 are alternately arranged in the form of a concentric circular band. However, this is merely exemplary and the arrangement is not limited thereto.

The optical module 110 may include a collimator 225 which collimates light, reflected or scattered from the object OBJ, in a direction of the detector 112. In this case, the collimator 225 may include an optical lens, and the like.

A lower portion of the optical module 110 which contacts or faces the object OBJ may be made of an anti-reflection coated glass.

In addition, the optical module 110 may further include a wavelength control module for controlling a peat wavelength band of a light source. The wavelength control module may be disposed on a rear surface of each light source 111 in order to independently control a peak wavelength of the light source 111. In this case, the wavelength control module may be a temperature adjustment member, for example, a resistance heating element or a thermoelement, which controls a peak wavelength by adjusting temperature of each light source 111, but is not limited thereto. Wavelength controller modules may be mounted in a manner that allows the wavelength controller modules to be detached from the respective light sources 111, or may be integrally formed with the light sources 111.

The pressure sensor 120 may continuously measure pressure between the optical module 110 and the object while the optical module 110 operates for measuring bio-information. In this case, the pressure sensor 120 may include a force sensor which measures contact pressure of the optical module and the object when measuring bio-information, such as a strain gauge, a piezoresistive pressure sensor, a capacitive pressure sensor, and the like, but is not limited thereto.

Referring to FIGS. 2A and 2C, the bio-information measuring apparatus 100 may further include an external frame 10 which supports the optical module 110, so that the optical module 110 is disposed inside the external frame 10.

One or more of the pressure sensors 120 may be disposed on one surface of the first direction change part 230 of the optical module 110, e.g., on a portion of non-light transmitting material which contacts or faces the object OBJ, as illustrated in FIG. 2A. In this case, a total of four pressure sensors $P_1$, $P_2$, $P_3$, and $P_4$ may be respectively disposed on each of four quadrants of the first direction change part 230, which is in the form of a concentric circle, as illustrated in FIG. 2B. In another example, the pressure sensor 120 may be disposed on a surface where the external frame 10 contacts or faces the object OBJ as illustrated in FIG. 2C. In this case, a total of four pressure sensors $P_1$, $P_2$, $P_3$, and $P_4$ may be disposed in the form of a concentric circle on the external frame 10.

The processor 130 is mounted in an inner space where the external frame 10 is formed, and may be electrically connected with the optical module 110. Upon receiving a request for measuring bio-information, the processor 130 may control the optical module 110. In the case where the optical module 110 is provided with a plurality of light sources, the optical module 110 may turn on/off each light source by time-dividing the light sources. The processor 130 may drive each light source based on driving conditions such as a current intensity, a pulse duration, and the like, of each light source. However, the processor 130 is not limited thereto, and nay turn on the plurality of light sources all together so that the light sources may emit light at the same time.

Figure 3:
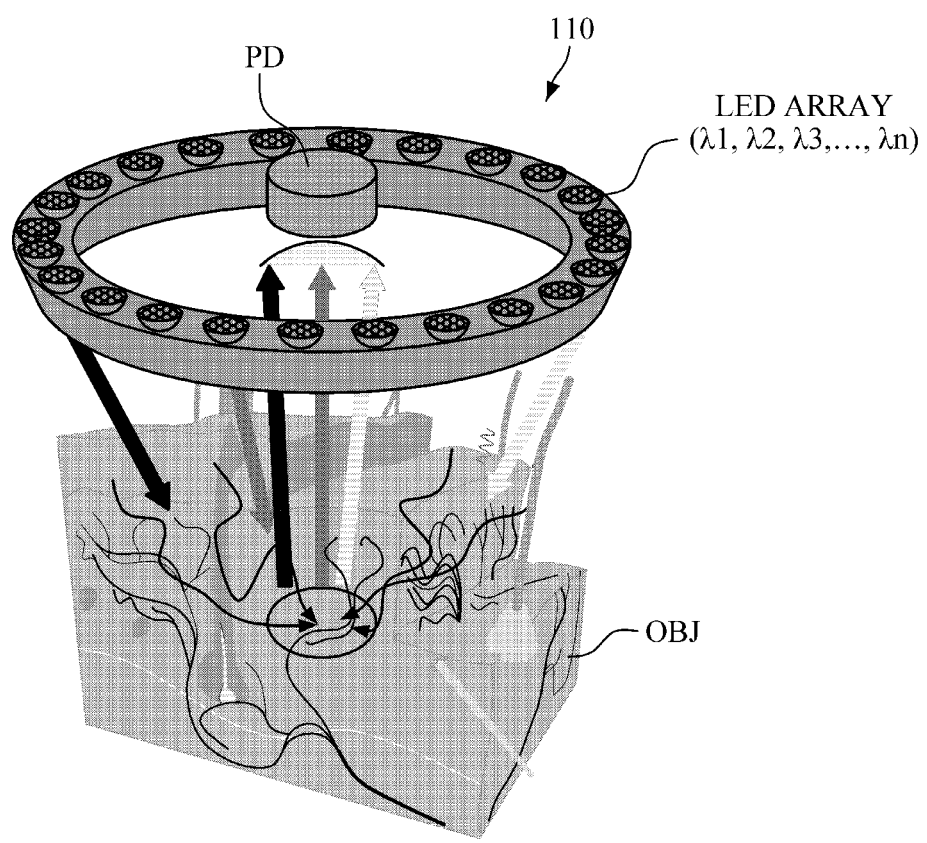
FIG. 3 is a diagram illustrating an example of an optical module having an LED array.

For example, FIG. 3 is a diagram illustrating an example of an optical module having an LED array. Referring to FIG. 3, the optical module 110 may include a photodiode PD at the center thereof, and n number of LEDs may be disposed in the form of a concentric circle around the photodiode PD. The LEDs may be preset to have different peak wavelengths $\lambda_1, \lambda_2, \lambda_3, \ldots,$ and $\lambda_n$. For example, even if some of the light sources are set to have the same temperature, the light sources may have different peak wavelengths by shifting the peak wavelengths by adjusting in detail the current intensity, the pulse duration, and the like, of the light sources.

In the case where a wavelength control module for each light source is disposed in the optical module 110, the processor 130 may individually control the wavelength control module for each light source before driving each light source, thereby controlling the peak wavelength to be emitted by each light source.

Once the reflected or scattered light is detected at the optical module 110, the processor 130 may restore a spectrum, and may measure bio-information by using the restored spectrum. In this case, the bio-information may be blood glucose, triglyceride, cholesterol, calories, protein, uric acid, and the like.

For example, as illustrated in FIG. 3, in the case where a light source has an array of n number of LEDs, and the peak wavelength of each LED is set to $\lambda_1, \lambda_2, \lambda_3, \ldots,$ and $\lambda_n$, light sources are time-divided to be sequentially driven in a pulse mode based on a driving order and pulse duration of each LED, and the detector (PD) may detect light returning from the object OBJ.

The processor 130 may obtain a linearly independent equation based on a data set about the response of the object detected by the detector (PD) and may restore a spectrum based on the linearly independent equation. For example, the processor 130 may obtain a linear equation written in matrix form as represented by the following Equation 1, and may obtain a spectrum reconstructed by using a method of solving the linear equation.

$$Az = U \quad \text{[Equation 1]}$$

Herein, A is a matrix of reference spectrum properties measured according to driving conditions of each light source; U is a matrix of values actually measured by the detector according to driving conditions equally set for each light source; and z is a spectrum to be restored. In this case, there may be an ill-conditioned matrix A, in which a system value of Equation 1, which is a linear equation, may be incorrect, such that by using a solution to an inverse problem, a spectrum of an object may be reconstructed with no limitations on the resolution size of the spectrum, and with high accuracy by using a minimum number of used spectrum curves. In this case, the inverse problem may be solved by using the Tikhonov regularization method as represented by the following Equation 2.

$$(\alpha E + A^T A) Z_\alpha = A^T u$$

$$Z_\alpha = (\alpha E + A^T A)^{-1} A^T u \quad \text{[Equation 2]}$$

Herein, u is each component of a matrix U actually measured by the detector; E is a unit matrix; A is a kernel matrix, and a matrix of a reference spectrum measured for each light source according to driving conditions of the light sources; and α is a unit of noise removal. The Equation 2 may be solved by a known method, e.g., a least square method, which may be solved by using, for example, QR decomposition.

Figure 4A:
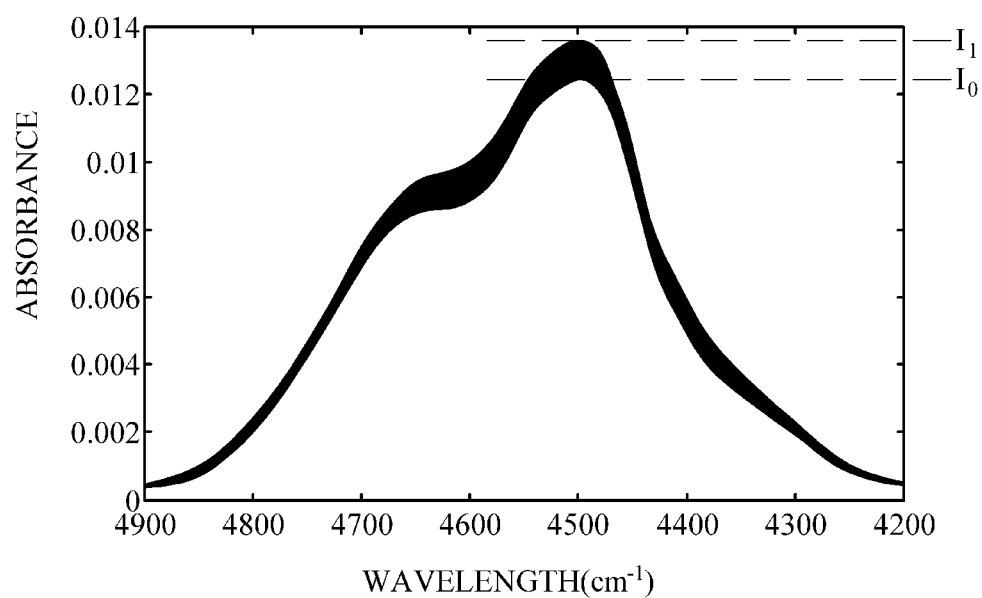
FIGS. 4A to 4C are diagrams explaining a spectrum change according to a change of pressure between an optical module and an object.
Figure 4B:
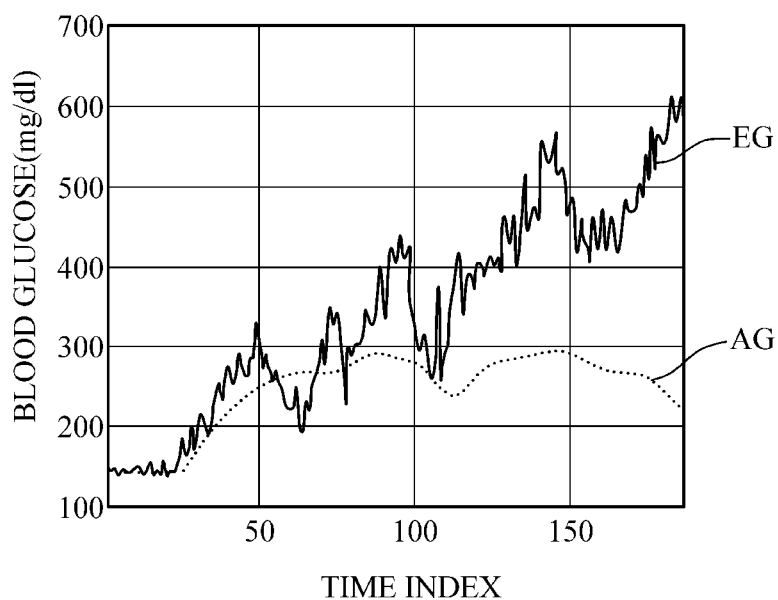
Figure 4C:
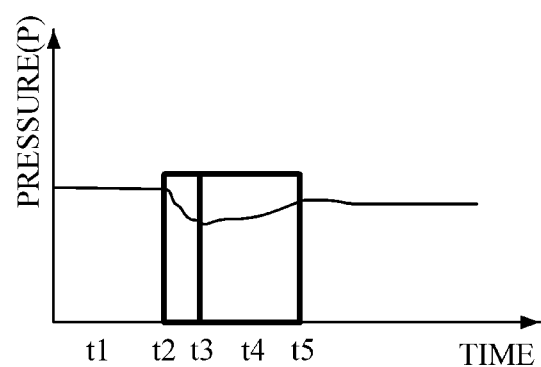

FIGS. 4A to 4C are diagrams explaining a spectrum change according to a change of pressure between an optical module and an object. As illustrated in FIG. 4A, in the case where bio-information is measured for a long period of time, a spectrum, e.g., absorbance may be changed from $I_0$ to $I_1$. Such spectrum change should be affected only by a change of biological component to be measured, for example, blood glucose component, but in practice, the spectrum change is also affected by a change of pressure between the optical module 110 and the object OBJ.

Referring to FIG. 4B, in the case where bio-information, e.g., blood glucose, is measured for a long period of time, difference gradually occurs between an estimated blood glucose (EG) level and an actual blood glucose (AG) level due to a pressure change in addition to the change of biological component, thereby leading to reduced accuracy.

Upon continuously receiving, from the pressure sensor 120, pressure information for a predetermined period of time when bio-information is measured, the processor 130 may correct a spectrum change, which occurs due to a pressure change, based on the continuously received pressure measurement values.

Upon restoring a spectrum during a predetermined period of time based on the reflected or scattered light detected by the optical module 110 for the predetermined period of time, the processor 130 may determine an event occurrence time when a pressure change occurs based on pressure measurement values continuously measured for the predetermined period of time.

For example, the processor 130 may compare a pressure measurement value at each measurement time with a pressure value at a reference time to obtain a difference therebetween; and may determine a time when the difference between the pressure values exceeds a threshold value to be an event occurrence time. In this case, the reference time may be a predetermined time, such as an initial measurement time, a time immediately before a time of determining whether an event occurs, and the like. Referring to FIG. 4C, assuming that a time of determining whether an event occurs is $t_3$, and a reference time is $t_2$ which is immediately before the time of determination, in the case where a pressure value at the time of determination $t_3$ and a pressure value at the reference time $t_2$ exceeds a threshold value, the processor 130 may determine the time of determination $t_3$ to be an event occurrence time.

Upon determining the event occurrence time, the processor 130 may correct a spectrum at the event occurrence time by reference to a correction model. In this case, the correction model may be pre-defined in lookup table form or in the form of an equation algorithm such as the following Equation 3.

$$\Psi_t(\lambda) = f(P)\Phi_t(\lambda) \quad \text{[Equation 3]}$$

Herein, $\Psi_t(\lambda)$ denotes a spectrum conversion value at a wavelength λ and a time t; and f(P) denotes a correction function for pressure P. In this case, according to a definition of the function, the pressure P may refer to a pressure value at the time t, or may be a difference between a pressure value at the reference time and a pressure value at the time t. Further, $\Phi_t(\lambda)$ denotes a spectrum measurement value at the wavelength λ and the time t.

Upon correcting a spectrum at the event occurrence time, the processor 130 may measure bio-information by using the corrected spectrum. For example, the processor 130 may calculate absorbance by using the corrected spectrum and a reference spectrum as represented by the following Equation 4. In this case, the reference spectrum may be a spectrum measured by emitting light onto or toward an object made of 100% reflective material and by detecting light reflected from the object.

$$\text{Abs} = -\log \frac{I_m}{I_r} \quad \text{[Equation 4]}$$

Herein, Abs denotes absorbance, $I_m$ denotes an intensity of the corrected spectrum, and $I_r$ denotes an intensity of the reference spectrum.

Upon calculating absorbance, the processor 130 may measure bio-information by applying the calculated absorbance to a bio-information measurement model, in which the bio-information measurement model may be pre-defined as an equation algorithm.

Upon measuring bio-information, the processor 130 may provide, to a user, the bio-information measurement value, the restored spectrum, the corrected spectrum, warning information based on the bio-information measurement value, and the like.

Figure 5:
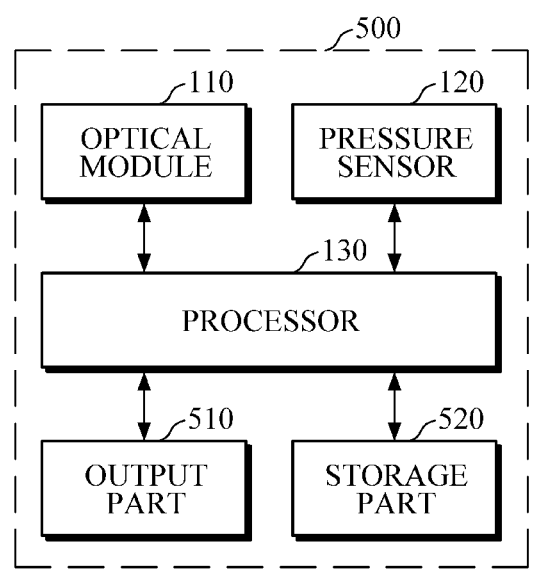
FIG. 5 is a block diagram illustrating a bio-information measuring apparatus according to another exemplary embodiment of the present disclosure.

FIG. 5 is a block diagram illustrating a bio-information measuring apparatus according to another exemplary embodiment of the present disclosure.

Referring to FIG. 5, the bio-information measuring apparatus 500 includes an optical module 110, a pressure sensor 120, a processor 130, an output part 510, and a storage part 520. The optical module 110, the pressure sensor 120, and the processor 130 are described above in detail with reference to FIGS. 1 to 4C, such that description below will be made based on details that do not overlap.

The output part 510 may output various types of information to a user under the control of the processor 130. The output part 510 is a hardware component. For example, once the processor 130 restores a spectrum, the output part 510 may visually output a graph of the restored spectrum to a display. Further, once the processor 130 corrects the restored spectrum, the output part 510 may visually output a graph of the corrected spectrum to a display. In this case, the restored spectrum and the corrected spectrum may be output together on one graph of time and intensity, in which different colors, different thickness and type of lines, and the like may be used to differentiate between the restored spectrum and the corrected spectrum.

Upon determining an event occurrence time by using the restored spectrum, the processor 130 may display an identification mark, e.g., an arrow, a figure such as a square, a circle, and the like, which indicate the event occurrence time, in a visual graph of the restored spectrum and/or the corrected spectrum.

Further, in response to a user's moving a time interval of the output graph forward and backward, the output part 130 may output a spectrum graph which corresponds to the time interval moved by the user, and may display an event occurrence time in the time interval.

The processor 130 may measure a state of contact between the optical module 110 and the object OBJ based on the pressure measurement value received from the pressure sensor 120. For example, in the case where two or more pressure sensors 120 are disposed facing each other, the processor 130 may determine the state of contact based on a difference between pressure measurement values of each pressure sensor 120.

Referring to FIGS. 2B and 2D, four pressure sensors $P_1$, $P_2$, $P_3$, and $P_4$ are disposed on the left and right and top and bottom sides. In this case, the processor 130 may calculate a difference between pressure measurement values of two pressure sensors ($P_i$ and $P_j$, i, j=1, 2, 3, 4, i≠j); and in the case where the calculated difference between pressure measurement values exceeds a threshold value, the processor 130 may determine that the state of contact is not normal. In this case, the threshold value may be pre-stored for each user in the storage part 520.

Upon determining that the state of contact is not normal, the processor 130 may generate warning information, in which the warning information may include haptic information such as a voice signal indicating an abnormal contact state, vibration, tactility, and the like. Further, the warning information may include visual information which displays a figure being turned on in red color on a display, or displays a difference between pressure measurement values of the pressure sensors $P_1$, $P_2$, $P_3$, and $P_4$.

Once the processor 130 generates the warning information about the contact state, the output part 510 may output the generated warning information to a user. As the warning information is output, the user may adjust the contact state by re-fastening the bio-information measuring apparatus 500 to an object.

The storage part 520 may store various types of reference information for measuring bio-information so as to be referred to by the processor 130. For example, the storage part 520 may store light source driving conditions including driving temperature, driving order, current intensity, pulse duration, and the like. The light source driving conditions may be pre-defined by considering measurement circumstances, such as a type of bio-information to be measured, a position to be examined and a state of an object, accuracy of bio-information measurement, performance of the optical module 110, a user's gender, age, health state, and the like, and may be updated by a user according to a change in the measurement circumstances.

Further, the storage part 520 may store information such as a threshold value for determining an event occurrence time, a threshold value for determining a contact state, and the like. In addition, the storage part 520 may store information such as a spectrum correction model, a bio-information measurement model, and the like. Moreover, the storage part 520 may store reference spectrum information required for calculation of absorbance.

The storage part 520 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 6:
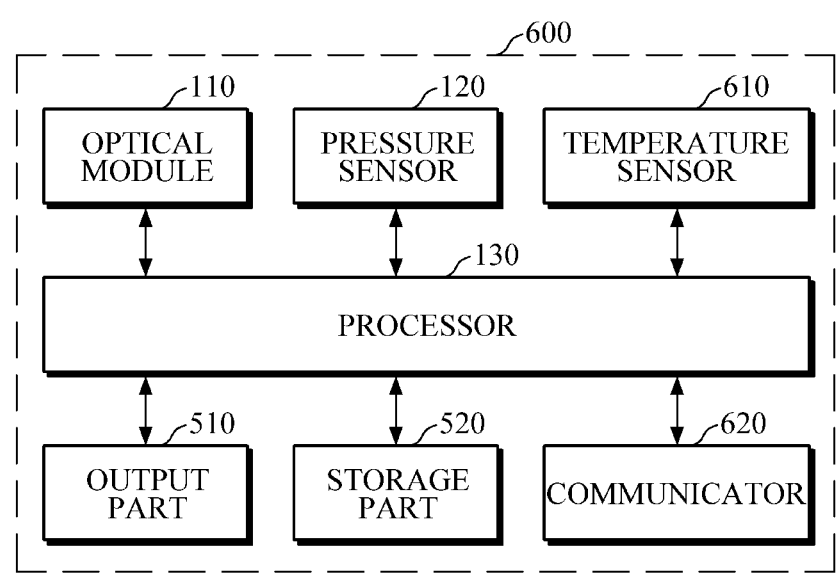
FIG. 6 is a block diagram illustrating a bio-information measuring apparatus according to yet another exemplary embodiment of the present disclosure.

FIG. 6 is a block diagram illustrating a bio-information measuring apparatus according to yet another exemplary embodiment of the present disclosure.

Referring to FIG. 6, the bio-information measuring apparatus 600 includes an optical module 110, a pressure sensor 120, a processor 130, an output part 510, a storage part 520, a temperature sensor 610, and a communicator 620. The optical module 110, the pressure sensor 120, the processor 130, the output part 510, and the storage part 520 are described above in detail with reference to FIGS. 1 to 5, such that description below will be made based on details that do not overlap.

The temperature sensor 610 may measure temperature of the object OBJ while the optical module 110 detects reflected or scattered light from the object OBJ. Referring to FIGS. 2A to 2D, the temperature sensor 610 may be disposed on one surface where the external frame 10 contacts or faces the object OBJ.

The processor 130 may be electrically connected with the temperature sensor 610, and upon receiving from the temperature sensor 610 temperature change information continuously measured while the reflected or scattered light from the object is detected, the processor 130 may correct a restored spectrum based on the received temperature change information. For example, in the case where a difference between temperature at a specific time and temperature at a reference time exceeds a threshold value, the processor 130 may determine the specific time to be an event occurrence time.

The processor 130 may correct the restored spectrum at the event occurrence time based on a correction model. In this case, the correction model may be pre-defined in lookup table form or in function form by considering a temperature change, or may be pre-defined by further reflecting a temperature change factor in the correction model which is based on a pressure change.

In addition, the processor 130 may determine a reference spectrum for calculating absorbance based on temperature information at a desired time to measure bio-information. For example, the reference spectrum may be measured for each temperature and may be stored in the storage part 520. The processor 130 may obtain the reference spectrum corresponding to measured temperature by reference to the storage part 520 based on the temperature information at the time of measuring bio-information, and may calculate absorbance based on the obtained reference spectrum and the corrected spectrum at the time of measuring bio-information.

The communicator 620 may transmit and receive various data by communicating with an external device under the control of the processor 130. For example, the communicator 620 may receive an actual blood glucose measurement value for calibrating a blood glucose model from a blood glucose measuring apparatus using an invasive method. Further, the communicator 620 may receive a reference spectrum for each temperature from a reference spectrum measuring apparatus. In addition, the communicator 620 may receive the above-described various types of reference information from an external device, and may transmit a measurement result of bio-information, the restored spectrum, the corrected spectrum, and the like to the external device. The external device may perform various functions for monitoring and managing a user's health by using the received bio-information measurement value and the like. The external device may be an information processing device, such as a bio-information measuring apparatus of an invasive type, a reference spectrum measuring apparatus, a smartphone, a tablet PC, a desktop computer, a laptop computer, and the like, which has a relatively high computing performance.

The communicator 620 may communicate with an external device by using a communication technique. In this case, the communication technique may include Bluetooth communication, Bluetooth Low Energy (BLE) communication, Near Field Communication (NFC), WLAN (WIFI) communication, Zigbee communication, Infrared Data Association (IrDA) communication, Wi-Fi Direct (WFD) communication, Ultra-Wideband (UWB) communication, Ant+ communication, WIFI communication, and mobile communication, but is not limited thereto.

Figure 7:
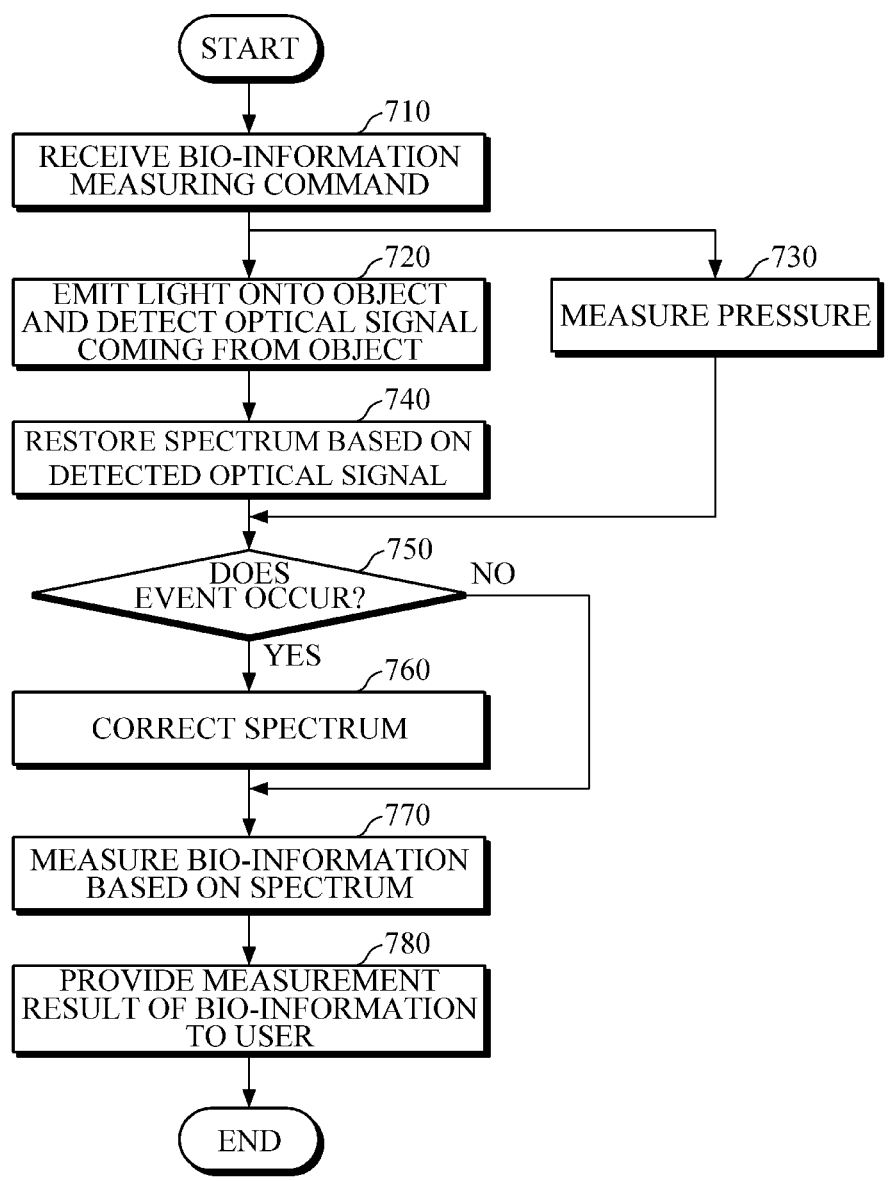
FIG. 7 is a flowchart illustrating a bio-information measuring method according to an exemplary embodiment of the present disclosure.

FIG. 7 is a flowchart illustrating a bio-information measuring method according to an exemplary embodiment of the present disclosure.

The bio-information measuring method of FIG. 7 may be an example of a bio-information measuring method performed by the bio-information measuring apparatus of FIG. 1.

Referring to FIG. 7, the bio-information measuring apparatus 100 may receive a bio-information measuring command (710). In this case, the bio-information measuring command may be input directly by a user or may be input via an external device.

Then, the bio-information measuring apparatus 100 may emit light onto or toward an object by controlling an optical module, and may detect reflected or scattered light coming from the object (720). The optical module may include one or more light sources and detectors. The light source may be one or more in number, and in the case where the light source is formed to be an array of a plurality of light sources, the bio-information measuring apparatus 100 may drive each light source by time-dividing the light sources.

In this case, the bio-information measuring apparatus 100 may measure pressure between the optical module and the object by using a pressure sensor (730). The pressure sensor may continue to measure pressure while operation 720 is performed.

Subsequently, the bio-information measuring apparatus 100 may restore a spectrum based on light reflected or scattered from the object and detected at the current time (740).

Next, the bio-information measuring apparatus 100 may determine whether an event occurs at the current time when the reflected or scattered light from the object is detected, based on the pressure measurement value measured by the pressure sensor (750). The bio-information measuring apparatus 100 may compare a pressure measurement value at the current time with a pressure measurement value at a reference time to obtain a difference therebetween, and if the obtained difference exceeds a threshold value, the bio-information measuring apparatus 100 may determine the current time to be an event occurrence time. In this case, the reference time may be a preset time, such as an initial measurement time, a time immediately before a time of determination on whether an event occurs, and the like.

Then, based on the determination in operation 750, if an event occurs at the current time, the bio-information measuring apparatus 100 may correct a spectrum (760) which is restored (740). For example, the bio-information measuring apparatus 100 may correct the spectrum by reference to a pre-defined correction model.

Subsequently, the bio-information measuring apparatus 100 may measure bio-information (770), by using the restored spectrum if an event does not occur at the current time, and by using the spectrum corrected (760) if an event occurs at the current time, based on the determination in operation 750. For example, the bio-information measuring apparatus 100 may calculate absorbance by using the measured reference spectrum, and the intensity of the corrected spectrum or the restored spectrum, and may measure bio-information by applying the calculated absorbance to a measurement model.

Next, the bio-information measuring apparatus 100 may output a measurement result of bio-information, and may provide the output measurement result of bio-information to a user (780). In this case, the bio-information measuring apparatus 100 may output the restored spectrum, the corrected spectrum, pressure information, warning information, and the like along with the measurement result of bio-information.

Figure 8:
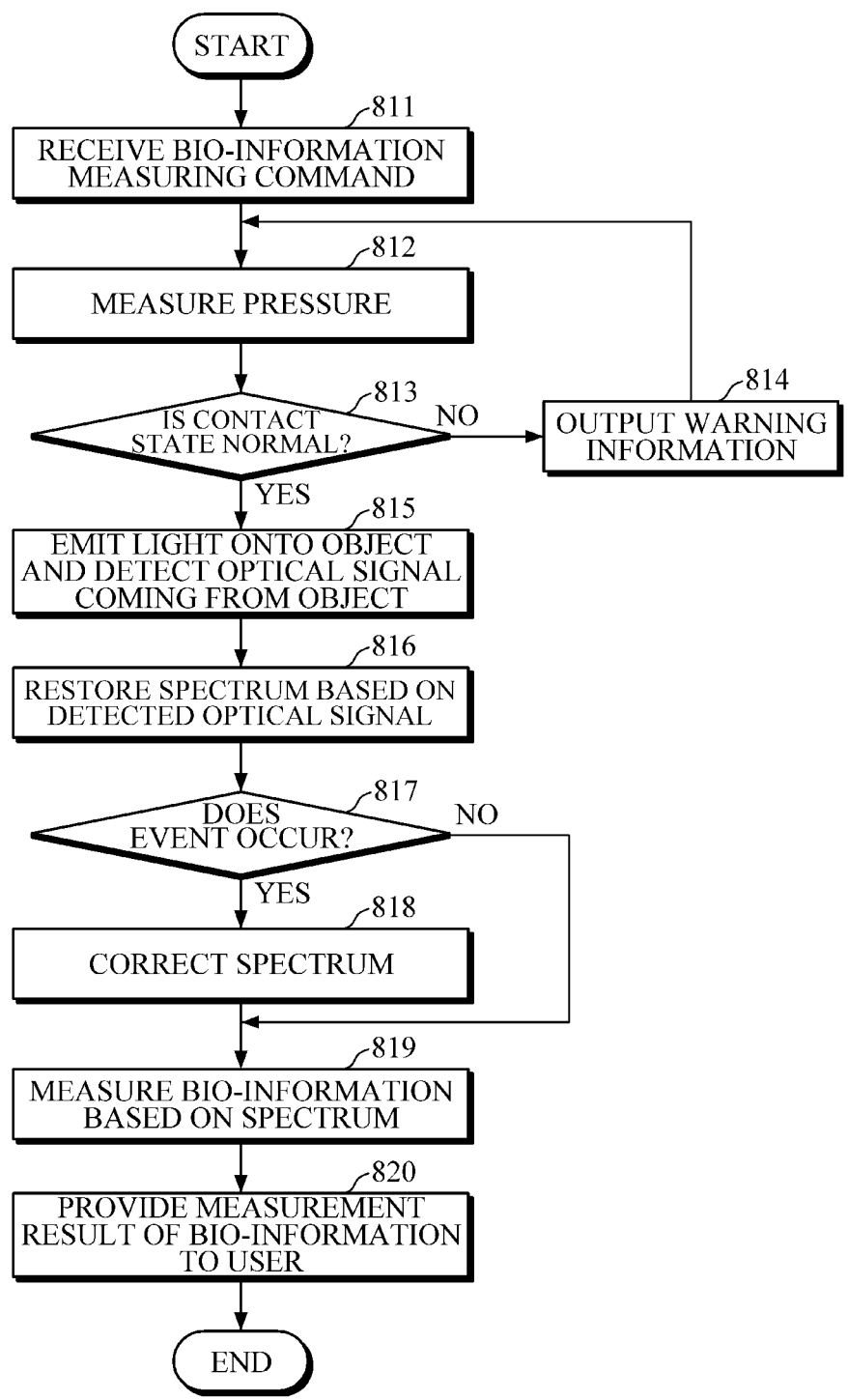
FIG. 8 is a flowchart illustrating a bio-information measuring method according to another exemplary embodiment of the present disclosure.

FIG. 8 is a flowchart illustrating a bio-information measuring method according to another exemplary embodiment of the present disclosure.

The bio-information measuring method of FIG. 8 may be a bio-information measuring method performed by the bio-information measuring apparatus of FIG. 5.

Referring to FIG. 8, upon receiving a bio-information measuring command (811), the bio-information measuring apparatus 500 may measure pressure by using a pressure sensor (812). In this case, a plurality of pressure sensors (812) may be disposed. For convenience of explanation, the measuring of pressure (812) is performed before the detecting of reflected or scattered light from the object (815) in FIG. 8, but the measuring of pressure (812) may be performed continuously while the detecting of reflected or scattered light from the object (815) is performed.

Then, the bio-information measuring apparatus 500 may determine a state of contact between an optical module and an object by using the measured pressure value (813). For example, the bio-information measuring apparatus 500 may calculate a difference between pressure values measured by a plurality of pressure sensors, and if the calculated difference between the pressure values exceeds a threshold value, the bio-information measuring apparatus 500 may determine that the state of contact is not normal.

Subsequently, based on the determination in operation 813, if the state of contact is not normal, the bio-information measuring apparatus 500 may output warning information (814). In this case, if a user adjusts a contact state by, for example, wearing again the bio-information measuring apparatus 500 and the like, the bio-information measuring apparatus 500 may repeat the measuring of pressure (812).

Next, based on the determination in operation 813, if the state of contact is normal, the bio-information measuring apparatus 500 may control the optical module to emit light onto or toward an object, and may detect the reflected or scattered light coming from the object (815).

Then, the bio-information measuring apparatus 500 may restore a spectrum based on the detected reflected or scattered light from the object in 816, and may determine whether an event occurs (817) based on the pressure value measured (812). For example, the bio-information measuring apparatus 500 may obtain a change of pressure values at the current time compared to a pressure value at a reference time, and may determine whether an event occurs at the current time.

Subsequently, based on the determination in operation 817, if the current time is an event occurrence time, the bin-information measuring apparatus 500 may correct the restored spectrum (818).

Next, the bio-information measuring apparatus 500 may measure bio-information based on the restored spectrum or the corrected spectrum (819). For example, the bin-information measuring apparatus 500 may calculate absorbance by using the intensity of the measured reference spectrum or the corrected spectrum, and may measure bio-information based on a measurement model.

Then, the bio-information measuring apparatus 500 may output a measurement result of bin-information, and may provide the output measurement result of Ho-information to a user (820).

Figure 9:
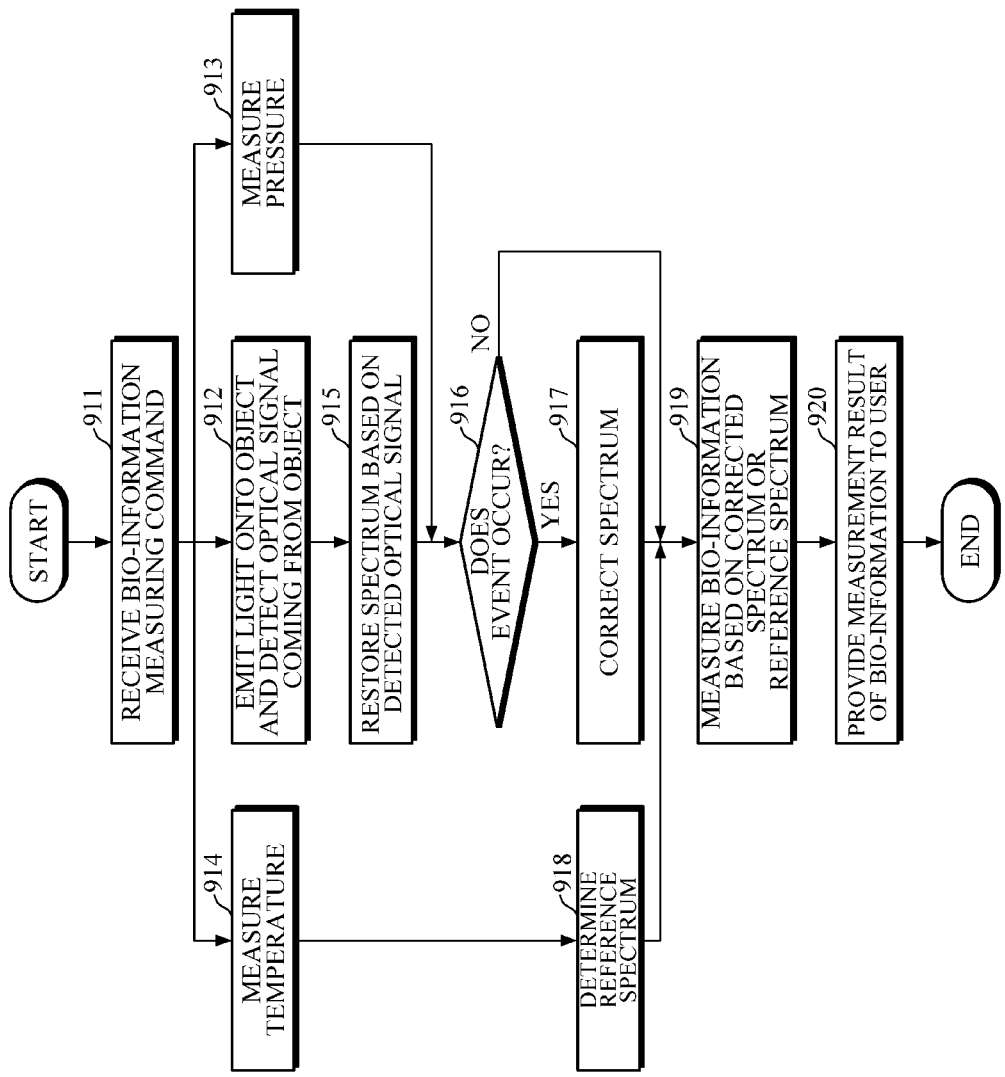
FIG. 9 is a flowchart illustrating a bio-information measuring method according to yet another exemplary embodiment of the present disclosure.

FIG. 9 is a flowchart illustrating a bio-information measuring method according to yet another exemplary embodiment of the present disclosure.

The bio-information measuring method of FIG. 9 may be an example of a bio-information measuring method performed by the bio-information measuring apparatus 600 of FIG. 6.

Referring to FIG. 9, the bio-information measuring apparatus 600 may receive a bio-information measuring command (911), and may control an optical signal to detect reflected or scattered light coming from the object (912).

In this case, the bio-information measuring apparatus 600 may measure pressure between the optical module and the object by using a pressure sensor (913). The pressure sensor may continue to measure pressure while the operation in 912 is performed.

Further, the bio-information measuring apparatus 600 may measure temperature of the object (914) by using a temperature sensor while the optical module detects light from the object.

Then, the bio-information measuring apparatus 600 may restore a spectrum based on the light coming from the object that is detected at the current time (915).

Next, the bio-information measuring apparatus 600 may determine whether an event occurs at the current time based on the pressure measurement value measured by the pressure sensor (916). For example, the bio-information measuring apparatus 600 may determine whether an event occurs at the current time by comparing a pressure measurement value at the current time with a pressure measurement value at a reference time.

Then, based on the determination operation 916, if the current time is an event occurrence time, the bio-information measuring apparatus 600 may correct the restored spectrum (917).

Upon measuring temperature (914), the bio-information measuring apparatus 600 may determine a reference spectrum for calculating absorbance based on the measured temperature (918). The determining of the reference spectrum (918) may be performed between the measuring of temperature (914) and the measuring of bio-information (919). In this case, the reference spectrum is pre-measured for each temperature, and the bio-information measuring apparatus 600 may determine the reference spectrum corresponding to the measured temperature among the reference spectrums measured for each temperature.

Subsequently, the bio-information measuring apparatus 600 may measure bio-information based on the restored spectrum or the corrected spectrum (919). For example, the bio-information measuring apparatus 600 may calculate absorbance by using the reference spectrum determined in operation 918, and the intensity of the corrected spectrum or the restored spectrum, and may measure bio-information based on the calculated absorbance and a measurement model.

Next, the bio-information measuring apparatus 600 may output a measurement result of bio-information and may provide the output measurement result of bio-information to a user (920). In this case, the bio-information measuring apparatus 600 may output the restored spectrum, the corrected spectrum, pressure information, temperature information, warning information, and the like along with the measurement result of bio-information.

Figure 10:
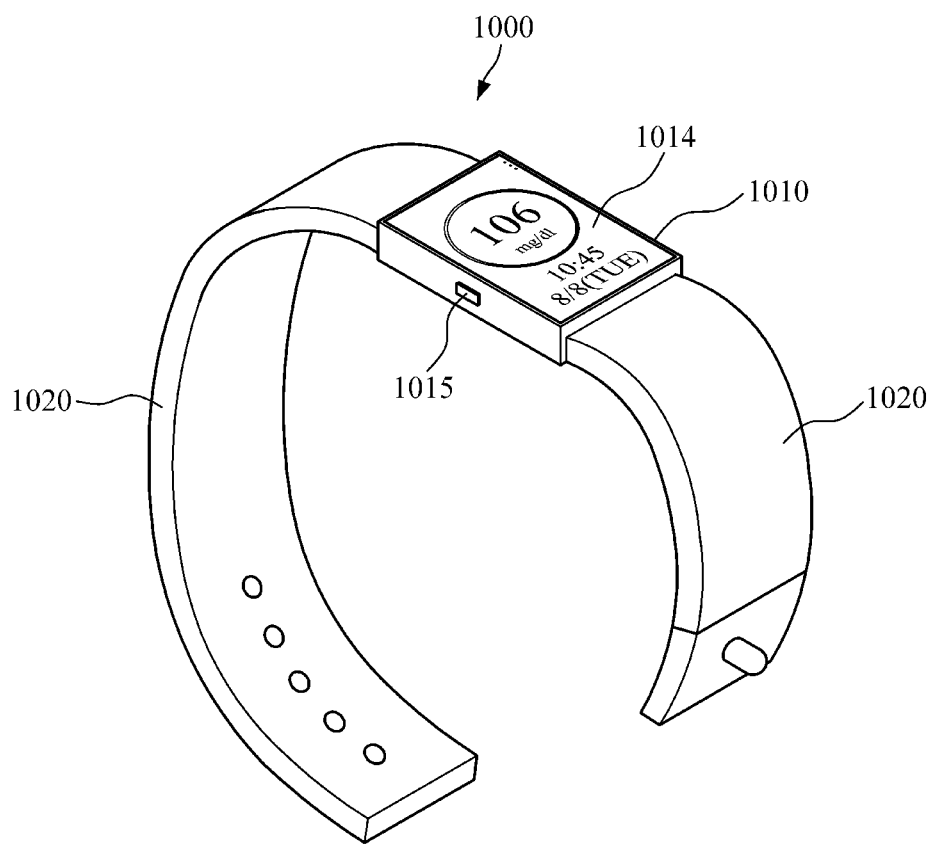
FIG. 10 is a diagram illustrating a wearable device according to an exemplary embodiment of the present disclosure.

FIG. 10 is a diagram illustrating a wearable device according to an exemplary embodiment of the present disclosure. FIG. 10 illustrates a smart watch-type wearable device worn on a user's wrist, as an exemplary embodiment of the above-described bio-information estimation apparatuses 100, 500, and 600.

Referring to FIG. 10, the wearable device 1000 includes a main body 1010 and a strap 1020. Various parts and functions of the bio-information estimation apparatuses 100, 500, and 600 may be mounted in or on the main body 1010 or may be exposed to the outside thereof.

The main body 1010 may be worn with the strap 1020 around a user's wrist, and the strap 1020 may be formed to be connected at both sides of the main body 1010 to be fastened to each other, or may be integrally formed as a smart band. The strap 1020 may be made of a flexible material to bend around a user's wrist so that the main body 1010 may be worn around a user's wrist.

The main body 1010 or the strap 1020 may include a battery which supplies power to the wearable device 1000.

The optical module may be provided at the bottom of the main body 1010 to be exposed to the wrist of a user, and may include a light source and a detector.

A pressure sensor may be mounted at a lower portion of a non-light transmitting material or at a portion of an external frame of the main body 1010 which surround the optical module. When the main body 1010 is worn a user's wrist, the pressure sensor may measure pressure between the optical module and wrist.

Further, a temperature sensor may be mounted on a portion of the external frame of the main body 1010 which surrounds the optical module. The temperature sensor may measure temperature of the wrist while the optical module detects reflected or scattered light coming from the object at the wrist.

A processor, which is mounted in the main body 1010, may process a user command input through a touch panel of a manipulator 1015 or a display 1014. For example, the processor may control the optical module to detect reflected or scattered light according to a bio-information measuring command of the optical module and a user, and may measure bio-information by restoring a spectrum based on the detected light from the object.

In this case, the processor may determine whether to correct the restored spectrum based on pressure information received from the pressure sensor, and if correction is required, the processor may correct the restored spectrum and may measure bio-information by using the corrected spectrum.

Upon receiving the pressure information from a plurality of pressure sensors, the processor may determine a contact state based on a difference between pressure values of the plurality of pressure sensors, and if the contact state is not normal, the processor may generate warning information so that a user may adjust a position of the main body 1010 or may re-fasten the strap 1020.

Further, upon receiving temperature information from the temperature sensor, the processor may determine a reference spectrum based on the received temperature information, and may measure bio-information by using the determined reference spectrum.

A communicator may be mounted in the main body 1010, and may transmit and receive data by communicating with an external device. For example, the communicator may transmit a bio-information measurement value to the external device so that the external device may monitor a health state of a user.

In addition, a display, which is mounted at the top of the main body 1010, may output a processing result of the processor, for example, a bio-information measurement value, the restored spectrum, the corrected spectrum, the pressure information, the temperature information, the warning information, and the like. Further, the display may transmit a user's command, which is input by touch, to the processor.

The wearable device 1000 may further include a manipulator 1015 which is mounted in the main body 1010. In an exemplary embodiment, the manipulator 1015 is a button or another user interface. The manipulator 1015 may be exposed to the outside at one side of the main body 1010, may receive a command input from a user, and may transmit the received command to the processor. The manipulator 1015 may have a function of turning on/off the wearable device 1000.

The present invention can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the present invention can be easily deduced by one of ordinary skill in the art.

What is claimed is:

1. A bio-information measuring apparatus, comprising:
    an optical module comprising a light source configured to emit light toward an object, and a detector configured to detect light reflected or scattered from the object;
    a pressure sensor configured to measure a pressure between the optical module and the object; and
    a processor configured to restore a spectrum based on the detected light reflected or scattered from the object, and to determine an event occurrence time based on changes of pressure values continuously measured by the pressure sensor, and to correct the restored spectrum at the event occurrence time based on a correction model.

2. The apparatus of claim 1, wherein:
    the light source comprises an array of a plurality of light sources, the plurality of light sources comprising at least one from among a light emitting diode (LED), a laser diode, and a fluorescent body; and
    the processor is further configured to sequentially drive the plurality of light sources by time-dividing the plurality of light sources based on at least one of a driving order and pulse durations of the plurality of light sources.

3. The apparatus of claim 1, wherein the optical module further comprises a direction change part, the direction change part comprising a surface which is configured to change a direction of light emitted by the light source, so that the light is directed toward the object.

4. The apparatus of claim 3, further comprising an external frame, wherein the light source and the detector of the optical module are disposed inside the external frame.

5. The apparatus of claim 4, wherein the pressure sensor comprises a plurality of pressure sensors which are disposed on a surface of the direction change part or on a surface of the external frame.

6. The apparatus of claim 5, wherein the processor is further configured to determine a state of contact between the optical module and the object based on differences between pressure values measured between the optical module and the object by the plurality of pressure sensors.

7. The apparatus of claim 6, wherein the determined state of contact indicates whether a contact between the optical module and the object is one of normal or not normal and the apparatus further comprises an output part configured to output warning information in response to the determined state of contact indicating that the contact between the optical module and the object is not normal.

8. The apparatus of claim 6, wherein the plurality of pressure sensors comprises at least two from among a strain gauge, a piezoresistive pressure sensor anti a capacitive pressure sensor.

9. The apparatus of claim 1, wherein the processor is further configured to determine the event occurrence time in response to a difference between a pressure value at a reference time and a pressure value at a measured time exceeding a threshold value.

10. The apparatus of claim 1, further comprising a temperature sensor configured to measure a temperature of the object when the optical module detects the light reflected or scattered from the object.

11. The apparatus of claim 10, wherein, from among a plurality of reference spectrums pre-measured for each of a plurality of temperatures, the processor is further configured to determine a reference spectrum for use in restoring the spectrum based on the temperature of the object measured by the temperature sensor.

12. The apparatus of claim 1, wherein the processor is further configured to measure bio-information, wherein the bio-information comprises at least one from among blood glucose, triglyceride, cholesterol, calories, protein, and uric acid, based on the corrected spectrum.

13. A bio-information measuring method, comprising:
    emitting light, by an optical module, toward an object and detecting, by a detector, light reflected or scattered from the object;
    measuring, by a pressure sensor, a pressure between the optical module and the object;
    restoring a spectrum based on the detected light reflected or scattered from the object;
    determining an event occurrence time based on changes of pressure values continuously measured by the pressure sensor; and
    correcting the restored spectrum at the event occurrence time based on a correction model.

14. The method of claim 13, wherein the pressure sensor includes a plurality of pressure sensors and the method further comprises:
    determining a state of contact between the optical module and the object based on differences between pressure values measured between the optical module and the object by the plurality of pressure sensors; and in response to the state of contact being determined as not being normal, outputting warning information.

15. The method of claim 13, wherein the determining of the event occurrence time comprises determining that an event occurs in response to a difference between a pressure value at a reference time and a pressure value at a measured time exceeding a threshold value.

16. The method of claim 13, further comprising:

measuring a temperature of the object when the optical module detects the light reflected or scattered from the object; and determining a reference spectrum based on the measured temperature.

17. The method of claim 13, further comprising measuring bio-information, the bio-information comprising at least one from among blood glucose, triglyceride, cholesterol, calories, protein, and uric acid, based on the corrected spectrum.

18. The method of claim 17, further comprising outputting a measurement result of the bio-information.

\* \* \* \* \*